(12) United States Patent
Woo

(10) Patent No.: US 9,351,817 B1
(45) Date of Patent: May 31, 2016

(54) DENTAL ANESTHETIC INJECTION DEVICE

(71) Applicant: Hee-Kyoung Woo, Seongnam-si (KR)

(72) Inventor: Hee-Kyoung Woo, Seongnam-si (KR)

( * ) Notice: Subject to any disclaimer, the term of this patent is extended or adjusted under 35 U.S.C. 154(b) by 0 days.

(21) Appl. No.: 14/979,579

(22) Filed: Dec. 28, 2015

(30) Foreign Application Priority Data

Dec. 1, 2015 (KR) ........................ 10-2015-0170170

(51) Int. Cl.
*A61M 5/307* (2006.01)
*A61C 19/08* (2006.01)
*A61M 5/30* (2006.01)
*A61N 5/067* (2006.01)

(52) U.S. Cl.
CPC .............. *A61C 19/08* (2013.01); *A61M 5/3007* (2013.01); *A61N 2005/067* (2013.01)

(58) Field of Classification Search
CPC .......... A61M 5/3007; A61N 2005/067; A61C 19/08
See application file for complete search history.

(56) References Cited

U.S. PATENT DOCUMENTS

| 6,251,099 B1* | 6/2001 | Kollias .................... A61N 1/325 604/20 |
| 6,689,094 B2* | 2/2004 | Kollias .................... A61N 1/325 604/69 |
| 2002/0007143 A1* | 1/2002 | Gordon .............. A61B 17/3203 604/70 |
| 2015/0011930 A1* | 1/2015 | Yamanishi ............. A61B 18/12 604/23 |
| 2015/0374920 A1* | 12/2015 | Perinchery .......... A61M 5/3015 604/20 |
| 2015/0374921 A1* | 12/2015 | Kojic ..................... A61M 5/30 239/1 |

FOREIGN PATENT DOCUMENTS

JP           3035448 U     12/1996
KR    10-2015-0100105 A    9/2015

* cited by examiner

*Primary Examiner* — Aarti B Berdichevsky
(74) *Attorney, Agent, or Firm* — Revolution IP, PLLC

(57) ABSTRACT

Disclosed herein is a dental anesthetic injection device. The dental anesthetic injection device includes a laser generator, a pressure generator filled with a liquid for generating pressure, which expands due to a laser emitted by the laser generator, an anesthetic container which contains an anesthetic for dental use, a separation film disposed between the pressure generator and the anesthetic container and formed to be elastically deformable to transfer expansion energy of the pressure generator to the anesthetic container, and a replacement nozzle detachably coupled with the anesthetic container to be replaceable depending on an oral environment and configured to jet the anesthetic of the anesthetic container toward an oral cavity.

5 Claims, 5 Drawing Sheets

DENTAL ANESTHETIC INJECTION DEVICE

CROSS-REFERENCE TO RELATED APPLICATION

This application claims priority to and the benefit of Korean Patent Application No. 10-2015-0170170, filed on Dec. 1, 2015, the disclosure of which is incorporated herein by reference in its entirety.

BACKGROUND

1. Field of the Invention

The present invention relates to a dental anesthetic injection device, and more particularly, to a dental anesthetic injection device capable of controlling an anesthetic jet pattern.

2. Discussion of Related Art

Generally, as a method of parenterally injecting a therapeutic agent into a body of a patient, various drug delivery systems have been applied. Among such drug delivery systems, the most generally used method is to use syringes with a needle, in which a medication is directly injected beneath the skin using a syringe with an injection needle. However, dental anesthetic is injected into a particular skin different from general skin, such as oral mucosa, gingival sulcus, a pulp cavity, etc. That is, oral mucosa is covered with moist mucous membranes formed of protein such as mucin, etc. and a thin keratinous layer, gingival sulcus is a micro pocket-shaped structure having an area of several hundred micrometers in direct contact with scleroid teeth and constantly filled with an exudation and saliva, and a pulp cavity is a structure formed of soft tissue in teeth surrounded by hard enamel, an inside of which is a complex of blood vessels, nerves, and fibrous tissues and filled with lymph fluid and an exudation.

To an oral structure having an environment of such a particular structure, it is general to deliver anesthetic through a syringe. Accordingly, pain should necessarily occur, and it is necessary to develop an anesthetic delivery system capable of relieving such pain.

General microjet drug delivery apparatuses use a principal in which a liquid is injected from an end of a nozzle at a high speed and penetrates soft material such as the skin of a human being to deliver a liquid thereinto, which is effective when a surface is dry. However, general microjet drug delivery apparatuses deteriorate in penetrating power due to a liquid present on a surface of a pulp cavity formed of multiple tissues with irregular density, a surface of oral mucosa or an inside thereof which is already filled with another liquid. Since a drug is injected toward multiple tissues at a certain speed, weak tissues may be destroyed. Accordingly, it is impossible to effectively deliver dental anesthetic using conventional microjet drug delivery apparatuses and development for this is necessary.

SUMMARY OF THE INVENTION

Aspects of the present invention are as follows.

An aspect of the present invention is to provide a dental anesthetic injection device capable of controlling a depth of anesthetic-delivery to be uniform regardless of an oral environment of a human body.

Another aspect of the present invention is to provide a dental anesthetic injection device capable of minimizing shock and damage on oral tissues.

Still another aspect of the present invention is to provide a dental anesthetic injection device capable of minimizing interference caused by a liquid present above a tissue layer in an oral cavity.

Yet another aspect of the present invention is to provide a dental anesthetic injection device which has laser settings optimized for oral mucosa.

Aspects of the present invention are not limited thereto and additional aspects of the invention will be obvious to one of ordinary skill in the art from the following description.

According to one aspect of the present invention, there is provide a dental anesthetic injection device including a laser generator, a pressure generator filled with a liquid for generating pressure, which expands due to a laser emitted by the laser generator, an anesthetic container which contains an anesthetic for dental use, a separation film disposed between the pressure generator and the anesthetic container and formed to be elastically deformable to transfer expansion energy of the pressure generator to the anesthetic container, and a replacement nozzle detachably coupled with the anesthetic container to be replaceable depending on an oral environment and configured to jet the anesthetic of the anesthetic container toward an oral cavity, Detailed content of other embodiments will be described and illustrated in detailed description and drawings.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Figure 1:
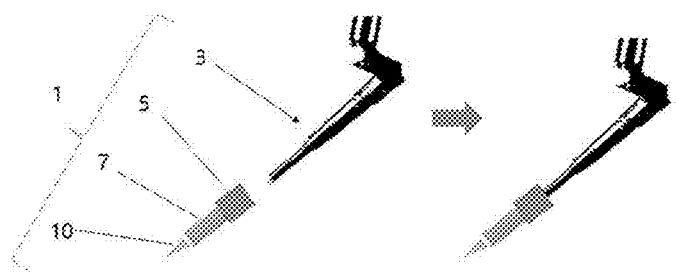
FIG. 1 is a conceptual view of a dental anesthetic injection device according to one embodiment of the present invention.

Advantages, features, and a method of achieving the same will be specified with reference to embodiments that will be described in detail with reference to the attached drawings.

However, the present invention should not be limited to the embodiments described below and may be embodied in various different forms. Merely, exemplary embodiments are provided to completely disclose the present invention and to allow one of ordinary skill in the art to fully understand the present invention. The present invention is defined only by the scope of claims thereof. Throughout the specification, like reference numerals designate like elements.

Hereinafter, a dental anesthetic injection device according to embodiments of the present invention will be described with reference to the drawings.

Figure 2:
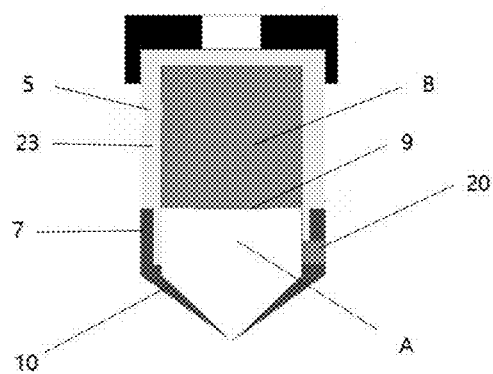
FIG. 2 is a longitudinal cross-sectional view of the dental anesthetic injection device according to one embodiment of the present invention.

FIG. 1 is a conceptual view of a dental anesthetic injection device (1) according to one embodiment of the present invention. FIG. 2 is a longitudinal cross-sectional view of the dental anesthetic injection device (1) according to one embodiment of the present invention.

Referring to FIGS. 1 and 2, the dental anesthetic injection device (1) according to one embodiment of the present invention includes a laser generator (3), a pressure generator (5) filled with a liquid for generating pressure, which expands due to a laser emitted by the laser generator (3), an anesthetic container (7) which contains dental anesthetic, a separation film (9) disposed between the pressure generator (5) and the anesthetic container (7) and formed to be elastically deformable to deliver expansion energy of the pressure generator (5) to the anesthetic container (7), and a replacement nozzle (10) which is detachably coupled with the anesthetic container (7) to be replaceable depending on an oral environment and jets an anesthetic A of the anesthetic container (7) toward an oral cavity.

The laser generator (3) may generate bubbles in the liquid by emitting the laser to the liquid.

The pressure generator (5) may contain the liquid and may include an internal space for containing the liquid therein. As an example, the liquid may be one of various liquefied materials such as a liquid, a sol, and a gel in which bubbles may occur, and most preferably water may be used. When water is used as the liquid, degassed water may be used to minimize deterioration in jet efficiency due to residual bubbles before and after laser emission and injection. Particularly, when a water soluble electrolyte, for example, salt is added to pure water, energy necessary for collapsing a structure of the liquid is reduced due to an effect of ionizing molecules, thereby further increasing the efficiency.

The separation film (9) may be disposed between the pressure generator (5) and the anesthetic container (7), and may expand or vibrate due to the generation or extinction of the bubbles. When the bubbles occur in the liquid, internal pressure of the pressure generator (5) may vary, thereby allowing the separation film (9) to expand or vibrate. Also, the bubbles which occur in the liquid directly collide with the separation film (9), thereby allowing the separation film (9) to expand or vibrate. When the separation film (9) expands or vibrates, a pressure may be applied to the anesthetic A and the anesthetic A may be jetted due to the pressure. As an example, the separation film (9) is a thin film type member and may be formed of an elastic material such as natural or synthetic rubber, but is not limited thereto. The separation film (9) may be formed of various materials which maintain a tightly stretched state but have elasticity to be deformable and restorable when receiving physical pressure from the outside.

The anesthetic container (7) may contain the anesthetic A, and may include an internal space for containing the anesthetic A therein. The anesthetic container (7) may be disposed adjacent to the pressure generator (5).

The anesthetic container (7) is connected to the replacement nozzle (10) which jets the anesthetic A. For example, the anesthetic container (7) may be disposed below the pressure generator (5), and the replacement nozzle (10) may be formed on one side of the anesthetic container (7). The anesthetic A may be an anesthetic solution in which the anesthetic A such as lidocaine is dissolved.

The anesthetic container (7) includes a rubber film (20), into which a needle of a syringe containing the anesthetic A is able to penetrate, on an outer circumferential surface thereof.

The needle of the syringe penetrates into the rubber film 20 and is inserted into the anesthetic container (7) to insert the anesthetic A into the anesthetic container (7).

Figure 3:
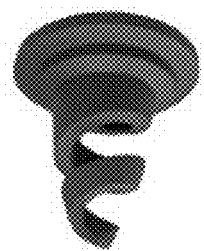
FIG. 3 is a perspective view of a spiral type replacement nozzle according to one embodiment of the present invention.

FIG. 3 is a perspective view of a spiral type replacement nozzle according to one embodiment of the present invention.

Figure 4:
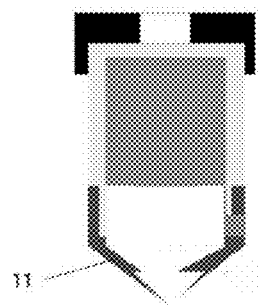
FIG. 4 is a longitudinal cross-sectional view of a dental anesthetic injection device according to another embodiment of the present invention, in which a spiral type replacement nozzle is mounted.

FIG. 4 is a longitudinal cross-sectional view of a dental anesthetic injection device according to another embodiment of the present invention, in which a spiral type replacement nozzle is mounted.

Figure 5:
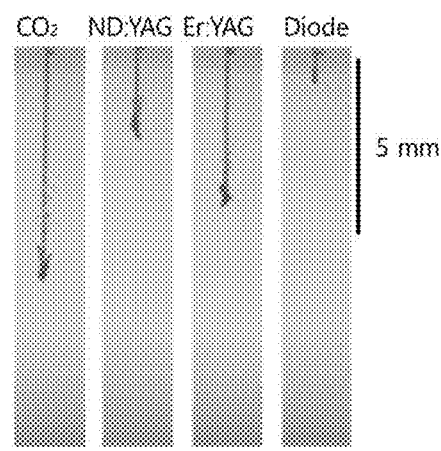
FIG. 5 illustrates an experimental result of measuring anesthetic-delivery depths depending on types of laser.

FIG. 5 illustrates an experimental result of measuring anesthetic A-delivery depths depending on types of laser. Experimental conditions are as follows. A laser emission time is 1.5 ms, the laser wavelength is 10 um, and the anesthetic A is a gelatin dye 1% solution in a lidocaine+1:100000 epinephrine solution.

In FIG. 5, the types of laser are a $CO_2$ laser, a neodymium-doped yttrium aluminum garnet (ND:YAG) laser, an erbium-doped yttrium aluminum garnet (Er:YAG) laser, and a diode laser, respectively.

The replacement nozzle (10) may include one of a conical flow channel, a radial flow channel, and a spiral flow channel formed therein. The spiral flow channel is formed to allow the anesthetic A which flows therein to be jetted after rotating three times to five times. For example, the replacement nozzle (10) may be a spiral type replacement nozzle (11). The spiral type replacement nozzle (11) includes a spiral flow channel formed therein to allow the jetted anesthetic A to have rotational energy.

The replacement nozzle (10) may control a jet pattern of the anesthetic A by changing a replacement nozzle type. For example, the jet pattern may mean a jet amount of the anesthetic A, a jet area of the anesthetic A, a jet velocity of the anesthetic A, and a jet method of the anesthetic A, such as jetting through one hole or a plurality of holes.

The replacement nozzle (10) may control a jet area on skin and a jet form of the anesthetic A. The replacement nozzle (10) may be a porous cylindrical shape which includes a plurality of flow channels. In this case, it is possible to jet the anesthetic A to several places of the skin at the same time.

The replacement nozzle (10) may be determined differently according to properties of an oral structure depending on oral mucosa, gingival sulcus, and a pulp cavity. A user may replace the replacement nozzle (10) to be appropriate for the oral structure. Each replacement nozzle (10) is detachably coupled with the anesthetic container (7). The replacement nozzle (10) includes threads and may be coupled with the anesthetic container (7).

The replacement nozzle (10) forms an inlet connected with the anesthetic container (7) and an outlet through which the anesthetic A is to be jetted toward a human body.

The replacement nozzle (10) may be one selected from a cylindrical type with a linear flow channel, a conical type with a linear flow channel which has a cross section reduced from an inlet toward an outlet, a radial type with a flow channel which has a cross section increasing from an inlet toward an outlet, and a spiral type with a spiral flow channel.

The replacement nozzle (10) may be a spiral type which rotates three times to five times while forming a spiral flow channel.

Since oral mucosa, gingival sulcus, a pulp cavity, etc. are constantly covered with water or mucous layers, it is impossible to appropriately deliver a drug by only jetting a liquid at a high speed. Also, a phenomenon in which a shock or damage is applied to tissues due to interference of liquids on the surface may occur. Accordingly, it is necessary for the user to select the replacement nozzle (10) which has a different drug delivery force depending on an oral state of a patient.

For example, the anesthetic A which passes through the spiral type replacement nozzle (11) has a rotational force. Accordingly, t the anesthetic A may more effectively penetrate into a skin layer. Accordingly, a drug-delivery depth increases. Accordingly, when the spiral type replacement nozzle (11) is selected, shock and damage to tissues may be prevented, and interference of liquids present on a tissue layer may be minimized.

Figure 6:
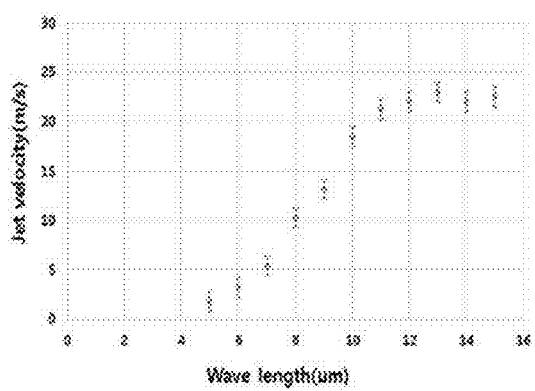
FIG. 6 is a graph illustrating anesthetic jet speed depending on a wavelength of a laser.

FIG. 6 is a graph illustrating a jet velocity of the anesthetic A depending on a wavelength of a laser. That is, it is a measurement photo. Experimental conditions are as follows. A laser type is $CO_2$, a laser emission time is 1.5 ms, and the anesthetic A is a gelatin dye 1% solution in a lidocaine+1:100000 epinephrine solution.

Figure 7:
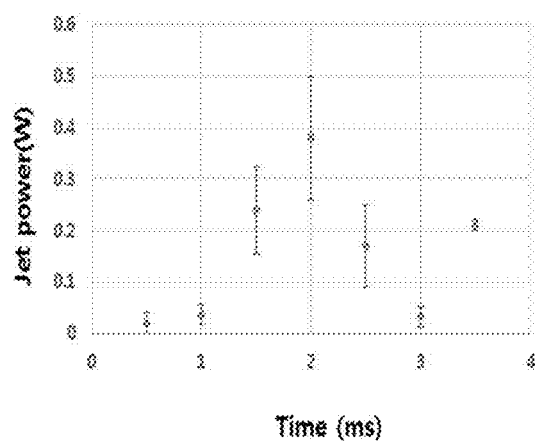
FIG. 7 is a graph illustrating anesthetic jet power for each emission time of a laser.

FIG. 7 is a graph illustrating anesthetic jet power for each emission time of a laser. Experimental conditions are as follows. A laser type is $CO_2$, a laser wavelength is 10 um, and the anesthetic A is a gelatin dye 1% solution in a lidocaine+1:100000 epinephrine solution.

Referring to FIGS. 6 and 7, the laser generator (3) generates a $CO_2$ laser with a lower energy wavelength than that of an Er:YAG laser. The laser generator (3) in which a laser emission time is set to be about 1.5 seconds to 2.5 seconds is preferable. An anesthetic may be inserted within the range of about 1.5 seconds to 2.5 seconds, and appropriate power of about 0.18 W may be generated.

The laser is appropriately the $CO_2$ laser. In the case of the Er:YAG laser, since an energy wavelength is high compared with the $CO_2$ laser, a drug may be instantaneously jetted at an excessively high velocity. Accordingly, in the case of an oral tissue which has a thin keratin layer and a loose inner cell layer, it is impossible to deliver the drug to an appropriate depth. Also, the $CO_2$ laser is generally used for a dental scaler or dental bleaching and is more economical and easily applicable than the Er:YAG laser.

A laser emitting time is preferably about 1.5 seconds to 2.5 seconds. Here, the anesthetic A is delivered to a depth of 3 mm to 10 mm which is the most appropriate depth.

The laser generator (3) may be preferably configured to emit the $CO_2$ laser. The $CO_2$ laser is a laser of high efficiency and large output and may heat a liquid to quickly generate bubbles in the liquid, thereby a jetting time of the anesthetic A may be minimized. To modify a wavelength and emission time of the laser emitted by the laser generator (3), the laser generator (3) may include a laser modifier (not shown) capable of modifying the wavelength and emission time of the laser.

For example, the laser modifier is a button type or a rotary type and may be configured to modify one or more of a wavelength and emission time of an emitted laser. For example, a wavelength of the $CO_2$ laser may preferably be about 8 um to 12 um. In the case of being within the range of about 8 um or more, since an anesthetic jet velocity may be 10 m/s or more, it is possible to quickly penetrate deep into the skin without damaging the skin. Also, the wavelength of the $CO_2$ laser may be preferably adjusted to 12 um or less. This is because anesthetic may cause damage to the skin.

The user may adjust a depth to which the anesthetic A is able to penetrate the skin by adjusting a wavelength and emission time of a laser. The emission time of the laser is adjusted, thereby adjusting a jet amount of the anesthetic A.

Figure 8:
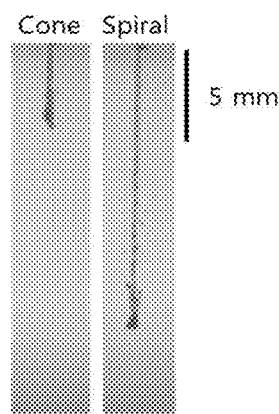
FIG. 8 illustrates an experimental result of measuring anesthetic-delivery depths depending on types of replacement nozzles.

Also, referring to FIG. 8, it may be seen that a penetration depth of the spiral type replacement nozzle (11) is greater compared with the conical type replacement nozzle (11). To allow an anesthetic agent to penetrate deeper, it is preferable to use the spiral type replacement nozzle (11).

Figure 9:
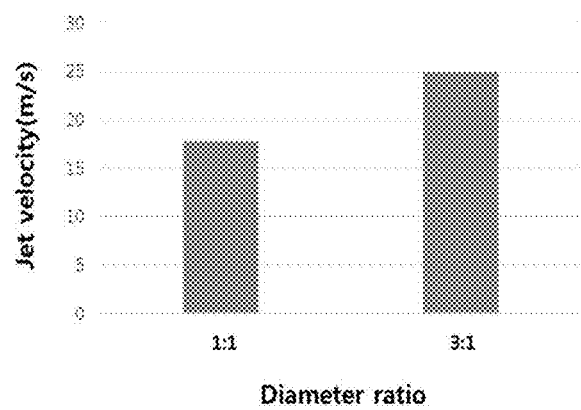
FIG. 9 illustrates an experimental result of measuring anesthetic jet speed according to a diameter ratio of a pressure generator to a separation film.

FIG. 9 illustrates an experimental result of measuring a jet velocity of the anesthetic A according to a diameter ratio of the pressure generator (5) with the separation film (9). Experimental conditions are as follows. A laser type is $CO_2$, a laser emission time is 1.5 ms, a laser wavelength is 10 um, and the anesthetic A is a gelatin dye 1% solution in a lidocaine+1:100000 epinephrine solution.

Referring to FIG. 9, the pressure generator (5) and the separation film (9) may be detachably coupled with the anesthetic container (7) to be replaceable with different diameters depending on an oral environment. The pressure generator (5) and the separation film (9) are formed at a diameter ratio of 1:1 to 3:1.

When a diameter of the pressure generator (5) to which a laser is emitted is 2 cm and a size of the separation film (9) is 2 cm, the diameter ratio is 1:1. In this case, an increase in a volume of liquid according to laser emission acts on a larger area of the separation film (9) than when the size of the separation film (9) is less than 2 cm. In this case, since energy output from the laser acts on the larger area of the separation film (9), energy transfer efficiency is reduced. That is, the jet velocity of the anesthetic is reduced. Meanwhile, when the diameter of the pressure generator (5) is 2 cm, the size of the separation film (9) is designed to be 0.5 cm to more efficiently transfer a volume expansion of a liquid portion vaporized by the laser to an elastic portion. Accordingly, pressure applied to a drug on a boundary between a drug deliverer and the separation film (9) may be more efficiently increased.

In detail, when the size of the separation film (9) was 2 cm and a ratio to the diameter of the pressure generator (5) was 1:1, a final jet velocity of the anesthetic A was about 18 m/s when the CO2 laser was emitted for 0.038 second. When the diameter was 0.5 and the ratio was 3:1, the jet velocity was 25 m/s when the same amount of energy was applied, which was faster. Since an anesthetic may be most efficiently inserted when the final jet velocity of the anesthetic is about 18 m/s to 25 m/s, the diameter ratio between the pressure generator (5) and the separation film (9) may be within the range from 1:1 to 3:1.

Also, when observed during the experimental procedure, the amount of the drug which dissipated through a gap between the separation film (9) and a drug container was reduced.

Effects of the present invention are as follows.

According to one embodiment of the present invention, a dental anesthetic injection device can control an anesthetic-delivery depth to be uniform regardless of an oral environment of a human body.

According to another embodiment of the present invention, a dental anesthetic injection device can minimize shock and damage on oral tissues.

According to still another embodiment of the present invention, a dental anesthetic injection device can minimize interference caused by a liquid present above a tissue layer in an oral cavity.

According to yet another embodiment of the present invention, a dental anesthetic injection device can have laser settings optimized for oral mucosa.

Effects of the present invention are not limited thereto and additional effects of the invention should be obvious to one of ordinary skill in the art from the following claims.

It should be apparent to those skilled in the art that various modifications may be made to the above-described exemplary embodiments of the present invention without departing from the spirit or scope of the invention. Thus, it is intended that the present invention covers all such modifications provided they come within the scope of the appended claims and their equivalents.

What is claimed is:

1. A dental anesthetic injection device comprising:
a laser generator;
a pressure generator filled with a liquid for generating pressure, which expands due to a laser emitted by the laser generator;
an anesthetic container which contains an anesthetic for dental use;
a separation film disposed between the pressure generator and the anesthetic container and formed to be elastically deformable to transfer expansion energy of the pressure generator to the anesthetic container; and
a replacement nozzle detachably coupled with the anesthetic container to be replaceable depending on an oral environment and configured to jet the anesthetic of the anesthetic container toward an oral cavity,
wherein the laser generator generates a $CO_2$ laser which has an energy wavelength lower than that of an erbium-doped yttrium aluminum garnet (Er:YAG) laser, and emits the $CO_2$ laser with a wavelength of 8 um to 12 um for 1.5 seconds to 2.5 seconds, and
wherein the replacement nozzle comprises a spiral flow channel to allow the jetted anesthetic to have rotational energy therein.

2. The dental anesthetic injection device of claim 1, wherein the spiral flow channel is formed to allow the anesthetic which flows therein to jet after rotating three times to five times.

3. The dental anesthetic injection device of claim 1, wherein the anesthetic container comprises a rubber film formed at an outer circumferential surface to allow a needle of a syringe which contains the anesthetic to penetrate thereinto.

4. The dental anesthetic injection device of claim 1, wherein the pressure generator and the separation film are detachably coupled with the anesthetic container to be replaceable in different diameters depending on the oral environment.

5. The dental anesthetic injection device of claim 4, wherein the pressure generator and the separation film are formed to have a diameter ratio therebetween within a range of 1:1 to 3:1.

* * * * *